United States Patent
Hirochika et al.

(10) Patent No.: US 8,076,547 B2
(45) Date of Patent: Dec. 13, 2011

(54) GENE REGULATING TILLERING AND LEAF MORPHOLOGY IN PLANT AND UTILIZATION OF THE SAME

(75) Inventors: Hirohiko Hirochika, Ibaraki (JP); Akio Miyao, Ibaraki (JP)

(73) Assignees: Incorporated Administrative Agency National Institute of Agrobiological Sciences, Ibaraki (JP); Incorporated Administrative Agency National Agriculture and Food Research Organization, Ibaraki (JP)

( * ) Notice: Subject to any disclaimer, the term of this patent is extended or adjusted under 35 U.S.C. 154(b) by 708 days.

(21) Appl. No.: 11/632,398

(22) PCT Filed: Jul. 15, 2004

(86) PCT No.: PCT/JP2004/010519
§ 371 (c)(1),
(2), (4) Date: Sep. 8, 2008

(87) PCT Pub. No.: WO2006/008822
PCT Pub. Date: Jan. 26, 2006

(65) Prior Publication Data
US 2009/0282578 A1 Nov. 12, 2009

(51) Int. Cl.
*C12N 15/82* (2006.01)

(52) U.S. Cl. .................................... 800/320; 800/278

(58) Field of Classification Search ................. None
See application file for complete search history.

(56) References Cited

FOREIGN PATENT DOCUMENTS
JP 2001-258574 A 9/2001

OTHER PUBLICATIONS

Kano-Murakami et al (1993, FEBS 334:365-368).*
Kikuchi et al., *Science*, 301(5631):376-379 (2003).
Masahiro Yano "Rice Genome Kozo to Kino Kaimei Saisentan", Kagaku to Sibutsu, 41(1):42-47 (2003) (No Translation available).
International Search Report for PCT Application PCT/JP2004/010519, Search Report dated Aug. 31, 2004, 3 pages (2004).
International Preliminary Report for Patentability for PCT Application PCT/JP2004/010519, 4 pages, English Translation (2004).

* cited by examiner

*Primary Examiner* — Stuart F. Baum
(74) *Attorney, Agent, or Firm* — King & Spalding LLP; Susan J. Myers Fitch; Peter J. Dehlinger

(57) ABSTRACT

It is intended to provide a polynucleotide encoding a gene capable of regulating tillering and leaf morphology in a plant and a method of regulating the phenotype of a plant by using this polynucleotide. The above-described polynucleotide can regulate the number of leaves or roots per individual or leaf morphology (including the length, width and thickness of leaves). In an embodiment, the plant usable in the regulation of tillering and leaf morphology is a monocotyledon. In a preferred embodiment, the monocotyledon is a gramineae plant. In a still preferred embodiment, the gramineae plant is rice.

10 Claims, 8 Drawing Sheets

Genotype   +/-   -/-

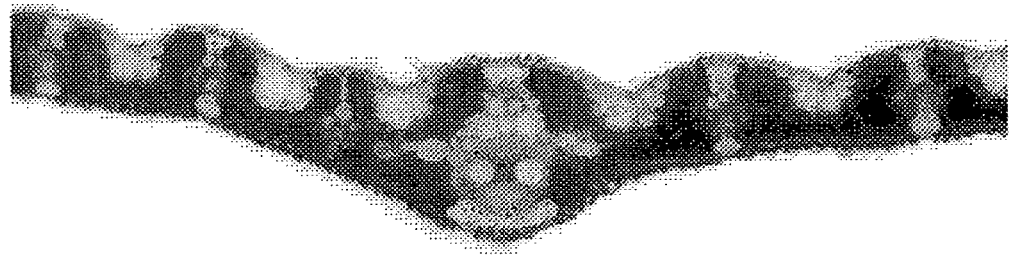
Fig.2  A NE3003(-/-)
B Nipponbare(control)

Probe: *Tos17*/XbaI-BamHI

Results of southern analysis using cloned candidate genes as probe

The structure of a gene on PAC AP003237 derived from rice species chromosome 1 as well as the location of Tos17 inserted thereto.

```
>AP003237 DNA Oryza sativa (japonica cultivar-group) genomic DNA, chromosome 1, PAC
          clone:P0046E05.
          Length = 162776

Score =  930 bits (469), Expect = 0.0
  Identities = 487/496 (98%)
  Strand = Plus / Minus Query: 1        tgtctgaccttatcctcataagaccaagtggcgcgccaagggctgtgttagctctccgag 60
                ||||||||||||||||||||||||||||||||||||||||||||||||||||||||||||
Sbjct: 112452   tgtctgaccttatcctcataagaccaagtggcgcgccaagggctgtgttagctctccgag 112393

Query: 61       gaacactgcttcagaagcccaccatcaagagagacctacaagatgatcttcgcttcctgg 120
                ||||||||||||||||||||||||||||||||||||||||||||||||||||||||||||
Sbjct: 112392   gaacactgcttcagaagcccaccatcaagagagacctacaagatgatcttcgcttcctgg 112333

Query: 121      tgtgggagagcttaaaaggatcagtcagatatattggcgcnnnnnnnnncactgaagacag 180
                ||||||||||||||||||||||||||||||||||||||||         |||||||||||
Sbjct: 112332   tgtgggagagcttaaaaggatcagtcagatatattggcgctttagaagcactgaagacag 112273

Query: 181      cagttgagaggtttggtagcgctaatgtcagtgttgctgggcactccttgggagctggat 240
                ||||||||||||||||||||||||||||||||||||||||||||||||||||||||||||
Sbjct: 112272   cagttgagaggtttggtagcgctaatgtcagtgttgctgggcactccttgggagctggat 112213

Query: 241      ttgctcttcaggtttgcaaagagctcgctaagcaaggagtcttcgtggagtgtcatctgt 300
                ||||||||||||||||||||||||||||||||||||||||||||||||||||||||||||
Sbjct: 112212   ttgctcttcaggtttgcaaagagctcgctaagcaaggagtcttcgtggagtgtcatctgt 112153

Query: 301      tcaatccaccttctgtttcacttgccatgggtgtaaggagtatgagtgagaaggccagct 360
                ||||||||||||||||||||||||||||||||||||||||||||||||||||||||||||
Sbjct: 112152   tcaatccaccttctgtttcacttgccatgggtgtaaggagtatgagtgagaaggccagct 112093

Query: 361      acctgtggaaaaaagttaaggctagtctaccactgactgaagaagcattacctgacagta 420
                ||||||||||||||||||||||||||||||||||||||||||||||||||||||||||||
Sbjct: 112092   acctgtggaaaaaagttaaggctagtctaccactgactgaagaagcattacctgacagta 112033

Query: 421      ccaaagaggagggaagtgcanagaagaaattgcgtgctgacaagaaatgggtgccacatt 480
                |||||||||||||||||||| |||||||||||||||||||||||||||||||||||||||
Sbjct: 112032   ccaaagaggagggaagtgcaaagaagaaattgcgtgctgacaagaaatgggtgccacatt 111973

Query: 481      tatatgtaaacaacag 496
                ||||||||||||||||
Sbjct: 111972   tatatgtaaacaacag 111957
```

Fig.6

Identification of a region homologous to the isolated flanking base sequence (Query).

CLUSTAL W (1.8) multiple sequence alignment

```
BAB67914.1    MAIDLAPLAGELEVAGAAVGGKKEEGEGEEGGVCGGEAVVVAAADAEVEGHPYDFHVSGP
AAD29063.1    ------------------------------------------MASDREEFNLCGP
                                                         :..  :*::.**

BAB67914.1    RNLPPPNWREIIRSSWKDPNYKRMVMACFIQAVYLLELDRQDEKGEEDGLAPKWWKPFKY
AAD29063.1    THLTT--------VDWGNEDHQRCVAACLVQGIYIVEQDRQLKREGTEALASPWWESFNF
              :*..         .* : :::* * **::*.:*::* *** ::   :.**. **:.*::

BAB67914.1    KVTQTLVDERDGSIYGAVLEWDRSSALSDLILIRPSGAPRAVLALRGTLLQKPTIKRDLQ
AAD29063.1    KLIRHLKDDADFSIFGGIFEYK-----SLQPDVVDSGVPRYVIAFRGTLTKADSITRDIE
              *: : * *:  * **:*.::*:.      *   :   **.** *:*:**** :  :*.**::

BAB67914.1    DDLRFLVWESLKGSVRYIGALEALKTAVERFGSANVSVAGHSLGAGFALQVCKELAKQGV
AAD29063.1    LDIHIIRNG-LHRTSRFEIAMQAVRSMADSVGASSFWLTGHSLGAAMALLAGKTMGKSGV
              *::::    *: : *: *::*:::  .:  .*::.. ::******. :**  . * :.*.**

BAB67914.1    FVECHLFNPPSVSLAMG--------VRSMSEKASYLWKK----VKASLPLTEEALPDSTKEEG
AAD29063.1    YIKSLLFNPPYVSPPIERIANERVRHGIRFAGSLITAGLALSRTLKQTQQPQQQQLQLQN
              ::: ***** **  .:        **   . *. *.     :. :* *::.  :. : :.

BAB67914.1    SAKKKLRADKKWVPHLYVNNSDYICCHYN-----------APNCSTTTTTTTTDGA
AAD29063.1    LTEDPLEALSSWLPNIHVNPGDHLCSEYIGFFEHRGNMEQIGYGAGIVERMAMQHSLGGL
              ::. *.*  ..:*::**  .*::**.*:.*        *   :  : .*

BAB67914.1    SDEQQQQRKASEIAG-----DVVAKLFVTSKGPQKFLEAHGLEQWWSDGMELQLAVYDSKL
AAD29063.1    LMDAMGVSNAVEVEEPVHVIPSANLIVNKTISEDYKDAHGIHQWWRDDQDLVSHIYMYK-
              :     :* *:     *:*:*... .:.: :***:.***  *.  :* *

BAB67914.1    IYRQLKSLYTATAPSPPAK
AAD29063.1    -------------------
```

Fig. 7

Sequence alignment results performed between a rice-derived enhanced tillering responsible gene (upper) and Arabidopsis-derived homologous gene (lower)

GENE REGULATING TILLERING AND LEAF MORPHOLOGY IN PLANT AND UTILIZATION OF THE SAME

This application is a U.S. National stage filing under 35 U.S.C. §371 of International Patent Application No. PCT/JP2004/010519, filed 15 Jul. 2004, which is incorporated herein by reference in its entirety.

REFERENCE TO SEQUENCE LISTING, TABLE OR COMPUTER PROGRAM

A "Substitute Sequence Listing" has been submitted with this application in the form of a text file, created 11 Jun. 2010 and modified 27 Apr. 2011, named 591508039SeqListApr2011.txt" (16,353 bytes), the contents of which are herein incorporated by reference in their entirety.

TECHNICAL FIELD

The present invention relates to a novel gene. More particularly, the present invention relates to a novel gene encoding a protein having a function of regulating tillering in plants.

BACKGROUND ART

A number of gene disruption strains (loss-of-function mutants) of rice have been produced by the property of rice retrotransposon Tos17 that is activated by culture to undergo transposition. Transposons are mutagenic genes which are ubiquitous in the genomes of animals, yeast, bacteria, and plants. Transposons are classified into two categories according to their transposition mechanism. Transposons of class II undergo transposition in the form of DNA without replication. Examples of class II transposons include Ac/Ds, Spm/dSpm and Mu elements of maize (*Zea mays*) (Fedoroff, 1989, Cell 56, 181-191; Fedoroff et al., 1983, Cell 35, 235-242; Schiefelbein et al., 1985, Proc. Natl. Acad. Sci. USA 82, 4783-4787), and Tam element of *Antirrhinum* (*Antirrhinum majus*) (Bonas et al., 1984, EMBO J. 3, 1015-1019). Class II transposons are widely used for gene isolation by means of transposon tagging. Such a technique utilizes a property of transposons, that is, a transposon transposes within a genome and enters a certain gene and, as a result, such a gene is physiologically and morphologically modified, whereby the phenotype controlled by the gene is changed. If such a phenotype change can be detected, the affected gene may be isolated (Bancroft et al., 1993, The Plant Cell, 5, 631-638; Colasanti et al., 1998, Cell, 93, 593-603; Gray et al., 1997, Cell, 89, 25-31; Keddie et al., 1998, The Plant Cell, 10, 877-887; and Whitham et al., 1994, Cell, 78, 1101-1115).

Transposons of class I are also called retrotransposons. Retrotransposons undergo replicative transposition through RNA as an intermediate. A class I transposon was originally identified and characterized in *Drosophila* and yeast. A recent study has revealed that retrotransposons are ubiquitous and dominant in plant genomes (Bennetzen, 1996, Trends Microbiolo., 4, 347-353; Voytas, 1996, Science, 274, 737-738). It appears that most retrotransposons are integratable but non-transposable units. Recently, it has been reported that some retrotransposons of such a type are activated under stress conditions, such as injury, pathogen attack, and cell culture (Grandbastien, 1998, Trends in Plant Science, 3, 181-187; Wessler, 1996, Curr. Biol., 6, 959-961; Wessler et al., 1995, Curr. Opin. Genet. Devel., 5, 814-821). For example, such activation under stress conditions was found in retrotransposons of tobacco, Tnt1A and Tto1 (Pouteau et al., 1994, Plant J., 5, 535-542; Takeda et al., 1988, Plant Mol. Biol., 36, 365-376), and rice, Tos17 (Hirochlka et al., 1996, Proc. Natl. Acad. Sci. USA, 93, 7783-7788).

The rice retrotransposon Tos17 is a class I element in plants that has been extensively studied. Tos17 was cloned by RT-PCR using degenerate primers prepared based on a conserved amino acid sequence of the reverse transcriptase domains of Ty1-copia group retro-elements (Hirochika et al., 1992, Mol. Gen. Genet., 233, 209-216). Tos17 has a length of 4.3 kb and has two identical LTRs (long terminal repeats) of 138 bp and a PBS (primer binding site) complementary to the 3' end of the initiator methionine tRNA (Hirochika et al., 1996, supra). Transcription of Tos17 is strongly activated by tissue culture, and the copy number of Tos17 increases with time in culture. Its initial copy number in Nipponbare (a Japonica variety), which is used as a genome research model, is two. In plants regenerated from tissue culture, its copy number is increased to 5 to 30 (Hirochika et al., 1996, supra). Unlike class II transposons found in yeast and *Drosophila*, Tos17 undergoes random transposition in chromosome and induces stable mutation. Therefore, Tos17 provides a useful tool in reverse genetics for analyzing the function of a gene in rice (Hirochika, 1997, Plant Mol. Biol. 35, 231-240; K. Shimamoto Ed., 1999, Molecular Biology of Rice, Springer-Verlag, 43-58; Miyao et. al., 2003, Plant Cell 15, 1771-1780).

DISCLOSURE OF THE INVENTION

The present inventors found mutants having increased tillering among a number of rice gene destruction lines which have been produced using the property of culture-activated rice retrotransposon Tos17. The inventors have identified and isolated the gene which cause the altered character of the mutant, thereby accomplishing the present invention.

In one aspect, the present invention provides a polynucleotide which encodes a plant gene capable of regulating tillering and leaf morphology in the plant, wherein the polynucleotide includes a polynucleotide which has a nucleotide sequence encoding an amino acid sequence from methionine (Met) at position 1 to lysine (Lys) at position 411 of SEQ ID NO: 2 as shown in the sequence listing; or which has a nucleotide sequence encoding the amino acid sequence having one or several amino acid deletions, substitutions and/or additions and is capable of regulating tillering and leaf morphology in the plant.

In another aspect, the present invention provides a polynucleotide which encodes a plant gene capable of regulating tillering and leaf morphology in the plant, wherein the polynucleotide has a nucleotide sequence from A at position 148 to G at position 1383; or nucleotide sequence capable of hybridizing to the nucleotide under stringent conditions.

In another aspect, the present invention provides A method for regulating tillering and leaf morphology in a plant, the method comprising: introducing a polynucleotide into a plant cell, wherein the polynucleotide encodes a plant gene capable of regulating tillering and leaf morphology in the plant, wherein the polynucleotide includes a polynucleotide which has a nucleotide sequence encoding an amino acid sequence from methionine (Met) at position 1 to lysine (Lys) at position 411 of SEQ ID NO: 2 as shown in the sequence listing; or which has a nucleotide sequence encoding the amino acid sequence having one or several amino acid deletions, substitutions and/or additions and is capable of regulating tillering and leaf morphology in the plant.

In another aspect, the present invention provides method for regulating tillering and leaf morphology in a plant, the method comprising step of: introducing a polynucleotide into the cells of the plant, wherein the polynucleotide has a nucleotide sequence from A at position 148 to G at position 1383; or nucleotide sequence capable of hybridizing to the nucleotide under stringent condition.

In one embodiment, the present method comprises the step of regenerating plant cells to obtain a plant.

In one embodiment, the plant whose tillering and morphology is controlled by the present invention, is monocotyledon.

In preferred embodiment, the monocotyledon is a plant which belongs to Poaeae family.

In more preferred embodiment, the plant which belongs to Poaeae family is rice.

In another embodiment, the plant whose tillering and morphology is controlled by the present invention, is dicotyledon.

BRIEF DESCRIPTION OF THE DRAWINGS

FIG. 2 comprises two photographs, showing cross sections of leaves of NE3003 (upper) and wild-type (lower), respectively.

In FIG. 3, solid circles indicate lanes corresponding to phenotypes having enhanced tillering and narrower leaves. In those lanes, the position of developed dark color bands is indicated by the arrow. It indicates that the positions of the dark color bands (−/−) correspond to the lines having said phenotype.

In FIG. 4, solid circles indicate lanes corresponding to phenotypes having enhanced tillering and narrower leaves. In those lanes, the position of developed dark color bands is indicated by the arrow. This strongly suggests that the cloned gene is the responsible gene.

FIG. 6 is an illustration showing the identification of a region homologous to the isolated flanking base sequence (Query; SEQ ID NO: 10). The first base of the flanking base sequence corresponds to the base next to the 3' terminal of Tos17. This indicates that Tos17 is inserted into the position of 112452 of AP003237 (SEQ ID NO: 12).

FIG. 7 shows sequence alignment results performed between a rice-derived enhanced tillering responsible gene (SEQ ID NO: 12) and *Arabidopsis*-derived homologous gene (SEQ ID NO: 13).

BEST MODE FOR CARRYING OUT THE INVENTION

Figure 1:
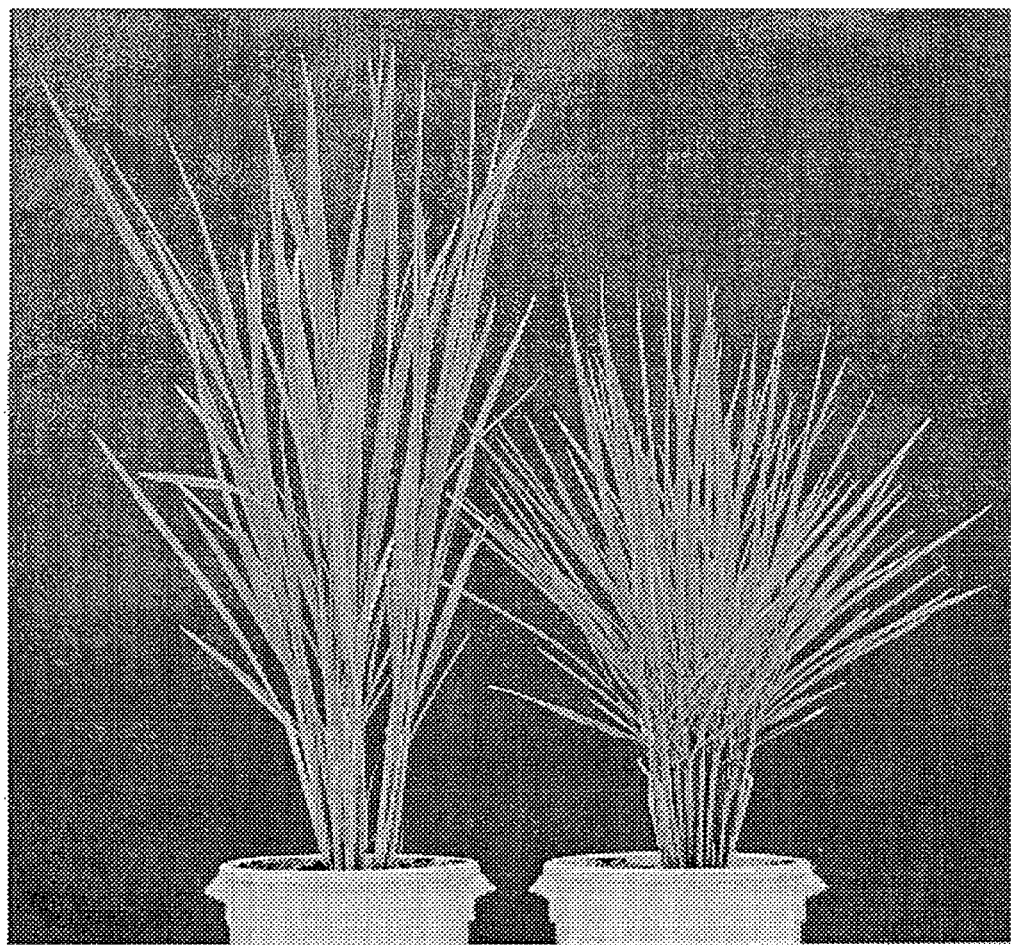
FIG. 1 is a photograph showing the morphology of a mutant and corresponding wild-type plant, where the mutant has increased tillering, and the wild-type plant is used as control.

The present invention provides a novel plant gene and method for regulating morphology in a plant, wherein the novel gene has been isolated by using To17 and its function has been elucidated.

As used herein, the term "gene" refers to a structural unit carrying hereditary information, which is a determinant capable of defining a character. A gene may be defined as a hereditary functional unit specified by the base sequence of a certain region in polymer DNA or RNA. Therefore, a gene may be understood as a DNA or RNA which will be eventually translated into a protein, or a polynucleotide as a substance.

The present invention provides a polynucleotide encoding a plant gene for regulating tillering in a plant. As used herein, "tillering" comprises division into plants, and branching in arbitrary position on a stem. As used herein, "regulating tillering" or "controlling tillering" refers to promotion or repression of the tillering process in a plant, as defined above. Further, a polynucleotide of the present invention can regulate number of leaves and/or roots, as well as shape of leaves (including length, width, and thickness thereof).

The polynucleotide of the present invention as mentioned above is a polynucleotide, typically including a polynucleotide having a nucleotide sequence encoding an amino acid sequence from methionine (Met) at position 1 to Lysine (Lys) at position 411 in SEQ ID NO: 2 in the sequence listing, or a nucleotide sequence encoding an amino acid sequence wherein one or several amino acids have been deleted from, substituted in, and/or added to the above amino acid sequence. In one embodiment, the polynucleotide of the present invention is a polynucleotide having a nucleotide sequence at position 148-1383 of SEQ ID NO: 1 of the sequence listing. The polynucleotide of the present invention may further contain a nucleotide sequence (e.g., a non-translational region) out of (5' or 3' to) the above-described regions (the nucleotide sequence region encoding the amino acid sequence from methionine (Met) at position 1 to Lysine (Lys) at position 411 of SEQ ID NO: 2 or the nucleotide sequence region at position 233-961 of SEQ ID NO: 1). More preferably, the polynucleotide of the present invention consists of the full-length sequence at position 1-1553 of SEQ ID NO: 1. The polynucleotide of the present invention includes all degenerate isomers of SEQ ID NO: 1. The term "degenerate isomer" refers to DNA encoding the same polypeptide and having a degenerate codon(s). For example, for a DNA having the base sequence of SEQ ID NO: 1 in which a codon corresponding to a certain amino acid (e.g., Asn) thereof is AAC, a DNA in which the AAC is changed to the degenerate codon AAT is called a degenerate isomer.

The polynucleotide of the present invention has been obtained from rice genomic DNA using Tos17 as a marker based on the finding of a mutant of a rice gene having extremely increased tillering. Such rice retrotransposon Tos17 is activated by culture and undergoes transposition. Therefore, in one embodiment, the polynucleotide of the present invention is derived from rice.

Fragments and variants of the disclosed nucleotide sequences and proteins encoded thereby may be included in the present invention. The term "fragment" is intended to refer to a portion of a nucleotide sequence or a portion of an amino acid sequence, or a protein encoded thereby.

A fragment of a nucleotide sequence can encode a protein fragment having at least one functional biological properties of a native protein. A variant of a protein encoded by the polynucleotide of the present invention is intended to refer to a protein modified from the native protein by at least one amino acid deletion (truncation) or addition at the N and/or C terminus of the protein; at least one amino acid deletion or addition at least one site in the protein; or at least one amino acid substitution at least one site in the protein. Such a variant may be generated by genetic polymorphism or artificial modification, for example.

The protein encoded by the polynucleotide of the present invention may be modified using various methods (including amino acid substitution, deletion, truncation, and insertion). These methods are generally known in the art. For example, a variant of the amino acid sequence of the protein encoded by the plant gene capable of controlling tilling of the present invention may be prepared by mutagenesis. Methods for mutagenesis and modification of a nucleotide sequence are well known in the art, e.g., Kunkel (1985) Proc. Natl. Acad. Sci. USA 82:488-492; Kunkel et al. (1987) Methods in Enzymol. 154:367-382; U.S. Pat. No. 4,873,192; Walker and Gaastra ed. (1983) Techniques in Molecular Biology (MacMillian Publishing Company, New York) and their cited references. Guidance for the selection of appropriate amino acid substitutions that do not affect biological activity of the protein of interest can be found in the model of Dayhoff et al. (1987) Atlas of Protein Sequence and Structure (Natl. Biomed. Res. Found. Washington, D.C.), which is herein incorporated by reference. Conservative substitution (e.g., one amino acid is substituted with another one having a similar property) may be preferable. Examples of such a substitution include a substitution between hydrophobic amino acids (Ala, Ile, Leu, Met, Phe, Pro, Trp, Tyr, and Val); a substitution between hydrophilic amino acids (Arg, Asp, Asn, Cys, Glu, Gln, Gly, His, Lys, Ser, and Thr); a substitution between amino acids having an aliphatic side chain (Gly, Ala, Val, Leu, Ile, and Pro); a substitution between amino acids having a side chain containing a hydroxyl group (Ser, Thr, and Tyr); a substitution between amino acids having a side chain containing a sulfur atom (Cys and Met); a substitution between amino acids having a side chain containing carboxylic acid and amide (Asp, Asn, Glu, and Gln); a substitution between amino acids having a side chain containing a base (Arg, Lys, and His); and a substitution between amino acids having a aromatic side chain (His, Phe, Tyr, and Trp).

Therefore, "one or several deletions, substitutions and/or additions" refers to as many amino acid substitution(s), deletion(s) and/or addition(s) as those caused by genetic polymorphism or artificial modifications (including the above-described well-known methods). "One or several deletions, substitutions and/or additions" are any number of amino acids that may be deleted from, added to, and/or substituted in the amino acid sequence of the protein as long as a protein having such modifications still has the same function as the protein encoded by the polynucleotide of the present invention. It will be clearly understood by those skilled in the art that the influence of modifications, such as amino acid substitutions, deletions and/or additions, on activity may be dependent on the positions, extent, types, or the like of amino acids to be modified. Regarding the polynucleotide of the present invention, a number of amino acids may be deleted, substituted and/or added in the full-length amino acid sequence to satisfy the amino acid sequence identity defined below, as long as the function of the protein encoded by the polynucleotide of the present invention can be expressed, for example.

The polynucleotide encoding the plant gene capable of controlling tillering of the present invention includes a polynucleotide having a nucleotide sequence encoding an amino acid sequence having at least 60%, preferably at least 65%, more preferably at least 70%, more preferably at least 75%, even more preferably at least 80%, still more preferably at least 90%, still even more preferably at least 95%, and most preferably at least 99% sequence identity to the amino acid sequence from Met at position 1 to Lys at position 411 in SEQ ID NO: 2 of the sequence listing as long as it can similarly tillering.

The polynucleotide encoding the plant gene capable of controlling tillering of the present invention includes a polynucleotide having a nucleotide sequence having at least 70%, preferably at least 75%, more preferably at least 80%, even more preferably at least 85%, still more preferably at least 90%, still even more preferably at least 95%, and most preferably at least 99% sequence identity to the nucleotide sequence encoding the amino acid sequence from Met at position 1 to Lys at position 411 in SEQ ID NO: 2 of the sequence listing (preferably, a nucleotide sequence from A at position 148 to G at position 1383 in SEQ ID NO: 1) as long as it can similarly control tillering.

As used herein, a "reference sequence" refers to a defined sequence used as a basis for a sequence comparison. A reference sequence may be a subset or the whole of the specified sequence; for example, a segment of a full-length cDNA or gene sequence or a complete DNA or gene sequence.

As used herein, a "comparison window" includes reference to a contiguous and specified segment of a polynucleotide sequence, wherein the polynucleotide sequence in the comparison window may contain additions or deletions (i.e., gaps) compared to the reference sequence (which does not comprise additions or deletions) for optimal alignment of the two sequences. Generally, the comparison window comprises at least 20 contiguous nucleotides in length, and optionally can be 30, 40, 50, 100, or longer. Those skilled in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Global optimal alignment of a reference sequence (the sequence of the present invention) and a subject sequence is preferably determined by homology analysis using BLASTX (Altshul et al., 1997, Nucleic Acids Res., 25, 3389-3402). In sequence alignment, the reference and subject sequences are both DNA sequences. An RNA sequence can be compared by converting U's to T's. The result of the global sequence alignment is in percent identity. The sequence alignment may be conducted using default parameters in the program.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins, it is recognized that residue positions which are not identical often differ by conservative amino acid substitutions where amino acid residues are substituted with other amino acid residues with similar chemical properties (e.g. charge or hydrophobicity) and therefore do not change the functional properties of the molecule. Where sequences differ in conservative substitutions, the percentage of sequence identity may be adjusted upwards to correct for the conservative nature of the substitution. Sequences which differ by such conservative substitutions are said to have "sequence similarity" or "similarity". Means for making this adjustment are well-known to those skilled in the art. Typically this involves scoring a conservative substitution as a partial rather than a full mismatch, thereby increasing the sequence identity percentage. Thus, for example, where an identical amino acid is given a score of 1 and a non-conservative substitution is given a score of zero, a conservative substitution is given a score between zero and 1. The scoring of conservative substitutions is calculated with, e.g., the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may contain additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters Those skilled in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes means sequence identity of normally at least 60%, more preferably at least 70%, 80%, 90%, and most preferably at least 95%.

The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman et al., J. Mol. Biol. 48: 443 (1970). A peptide is substantially identical to a second peptide, for example, where the two peptides differ only by a conservative substitution. Peptides which are "substantially similar" share sequences as noted above except that residue positions which are not identical may differ by conservative amino acid changes.

Fragments of the plant gene nucleotide sequence of the present invention capable of controlling tillering, which encode a biologically active portion of a protein capable of controlling tillering, encode at least 15, 25, 30, 50, 100, 125, 150, 175, 200, or 225 contiguous amino acids, or the overall amino acids present in the full-length protein of the present invention (e.g., 411 amino acids of SEQ ID NO: 2). In general, a fragment of the plant gene nucleotide sequence capable of controlling tillering, which is used as a hybridization probe for a PCR primer, may not encode a biologically active portion of a protein capable of controlling tillering in plants.

Polynucleotides encoding a plant gene capable of controlling tillering derived from plants other than rice may be included in the scope of the present invention. Such a polynucleotide may be isolated by, for example, conducting PCR using a primer based on the full-length or a portion of a disclosed nucleotide sequence and the genomic DNA of a selected plant as a template, followed by screening of genomic DNA or cDNA libraries of the same plant using an amplified DNA fragment as a probe. In this manner, methods such as PCR, hybridization, and the like can be used to identify such sequences based on their sequence identity to the sequence set forth herein. Sequences isolated based on their sequence identity to the sequences set forth herein or to fragments thereof are encompassed by the present invention.

In a hybridization technique, all or part of a known nucleotide sequence is used as a probe which selectively hybridizes an other corresponding nucleotide sequence present in a group of cloned genomic DNA fragments or cDNA fragments derived from a selected organism (i.e., genomic libraries or cDNA libraries). The hybridization probe may be genomic DNA fragments, cDNA fragments, RNA fragments, or other oligonucleotides, and may be labeled with a detectable group (e.g., $^{32}P$) or any other detectable marker. Therefore, probes for hybridization can be made by labeling synthetic oligonucleotides based on the nucleotide sequence of the plant gene capable of controlling tillering of the present invention. Methods for preparation of probes for hybridization and construction of cDNA libraries and genomic libraries are generally known in the art and are disclosed in Sambrook et al. (1989) Molecular Cloning: A Laboratory Manual (2nd ed., Cold Spring Harbor Laboratory Press, Plainview, N.Y., which is herein incorporated by reference).

For example, all or a part of a nucleotide sequence encoding the plant gene capable of controlling tillering disclosed herein can be used as a probe hybridizable to the corresponding plant gene sequence capable of controlling tillering and messenger RNA thereof. To achieve specific hybridization under various conditions, such a probe is unique to the plant gene sequence capable of controlling tillering, and includes sequences having preferably at least about 10 nucleotides in length, and most preferably at least about 20 nucleotides in length. Such a probe can be used in PCR to amplify the plant gene sequence capable of controlling tillering derived from a selected organism.

Methods for PCR amplification are well known in the art (PCR Technology: Principles and Applications for DNA Amplification, HA Erlich ed., Freeman Press, New York, N.Y. (1992); PCR Protocols: A Guide to Methods and Applications, Innis, Gelfland, Snisky, and White ed., Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford, these are herein incorporated by reference). This technique can be used as a diagnostic assay to isolate additional encoding sequences from a desired organism or to determine the presence of an encoding sequence in an organism. The hybridization technique includes hybridization screening of plated DNA libraries (either plaques or colonys; e.g., Sambrook et al. (1989) Molecular Cloning: A Laboratory Manual (2nd ed., Cold Spring Harbor Laboratory Press, Plainview, N.Y.)).

The hybridization of the sequences may be conducted under stringent conditions. The terms "stringent conditions or stringent hybridization conditions" include reference to conditions under which a probe will hybridize to its target sequence, to a detectably greater degree than other sequences (e.g., at least 2-fold over background). Stringent conditions are sequence-dependent and will vary with different circumstances. By controlling the stringency of the hybridization and/or washing conditions, target sequences that are 100% complementary to the probe can be identified. Alternatively, stringency conditions can be adjusted to allow some mismatching in sequences so that lower degrees of similarity are detected. Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) (pH 7.0 to 8.3) and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents (e.g., formamide). Exemplary stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Examples of more stringent conditions include hybridization in 40 to 45% formamide, 1.0 M NaCl, 1% SDS at 37° C., and a wash in 0.5× to 1×SSC at 55 to 60° C. Examples of even more stringent conditions include hybridization in 50% formamide, 1 M NaCl, 1% SDS at 37° C., and a wash in 0.1×SSC at 60 to 65° C.

Specificity is typically the purpose of post-hybridization washes, the critical factors being the ionic strength and temperature of the final wash solution. For DNA-DNA hybrids, the $T_m$ can be approximated from the equation of Meinkoth and Wahl (1984), Anal. Biochem., 138: 267-284: $T_m$=81.5° C.+16.6(log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with at least 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those skilled in the art will understand that variations in the stringency of hybridization and/or wash solutions are inherently described. If the desired degree of mismatching results In a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen (1993), Laboratory Techniques in Biochemistry and Molecular Biology Hybridization with Nucleic Acid Probes, Part I, Chapter 2 (Elsevier, N.Y.); and Ausubel, et al., Eds. (1995), Current Protocols in Molecular Biology, Chapter 2 (Greene Publishing and Wiley-Interscience, New York). Also See, Sambrook et al. (1989) Molecular Cloning: A Laboratory Manual (2nd ed., Cold Spring Harbor Laboratory Press, Plainview, N.Y., which is herein incorporated by reference).

The base sequence of the obtained gene can be determined by a nucleotide sequence analysis method known in the art or a commercially available automated sequencer.

The polynucleotide of the present invention is typically obtained in accordance with a method set forth herein, or may be obtained by chemical synthesis based on the sequences described in the present invention. For example, the polynucleotide of the present invention may be synthesized using a polynucleotide synthesizer commercially available from Applied BioSystems, Inc. in accordance with the instructions provided by the manufacturer.

As stated above, a polynucleotide produced by a procedure such as genetic engineering or chemical synthesis can be examined as to whether the polynucleotide has the desired activity, i.e., the ability of controlling tillering, in essentially similar manner to the procedure described in Example 6. Specifically, complementation test can be carried out by using increased-tillering mutants produced by transposition of Tos17, wherein recovery form the mutant to wild-type phenotype, which has no enhanced tillering, confirms the polynucleotide has the desired activity.

The modification in the present polynucleotide allows controlling the morphology of leaves, thereby improving photosynthetic efficiency, yield, qualities of a product and the like.

The polynucleotide of the present invention may be ligated in a native or modified form with an appropriate plant expression vector using a method well known to those skilled in the art, and the vector may be introduced into a plant cell using a known gene recombination technique. "Preferably, the polynucleotide of the present invention can be introduced so as to suppress functions of an endogenous gene, wherein the introduction can be expected to have a disease-resistant plant". The gene is incorporated in the DNA of a plant cell. The DNA of a plant cell includes DNA contained within various organelles (e.g., mitochondria and chloroplasts) as well as chromosomes.

As used herein, a "plant expression vector" refers to a nucleic acid sequence to which various regulatory elements, such as a promoter which regulates expression of the gene of the present invention, are operatively linked in a host plant cell. The term "control sequence" as used herein refers to a DNA sequence having a functional promoter and any related transcription element (e.g., an enhancer, a CCAAT box, a TATA box, and a SPI site). The term "operably linked" as used herein indicates that a polynucleotide is linked to a regulatory element which regulates expression of a gene, such as a promoter or an enhancer, so that the gene can be expressed. The plant expression vector may preferably include plant gene promoters, terminators, drug-resistance genes, and enhancers. It is well known to those skilled in the art that expression vector and regulatory element types used may be changed depending on the host cell. A plant expression vector used in the present invention may have a T-DNA region. The T-DNA region can enhance the efficiency of gene introduction, particularly when *Agrobacterium* is used to transform a plant.

The term "plant gene promoter" as used herein refers to a promoter which is expressed in plants. A plant promoter fragment can be employed which will direct the polynucleotide expression of the present invention in all tissues of a regenerated plant. Examples of a promoter for structural expression include a promoter for nopaline synthase gene (Langridge, 1985, Plant Cell Rep. 4, 355), a promoter for producing cauliflower mosaic virus 19S-RNA (Guilley, 1982, Cell 30, 763), a promoter for producing cauliflower mosaic virus 35S-RNA (Odell, 1985, Nature 313, 810), rice actin promoter (Zhang, 1991, Plant Cell 3, 1155), a maize ubiquitin promoter (Cornejo 1993, Plant Mol. Biol. 23, 567), and a REXφ promoter (Mitsuhara, 1996, Plant Cell Physiol. 37, 49).

Alternatively, the plant promoter can direct expression of a polynucleotide of the present invention in a specific tissue or may be otherwise under more precise environmental or developmental control. Such promoters are herein referred to as "inducible" promoters. Examples of inducible promoters include promoters which are inducible by environmental conditions, such as light, low temperature, high temperature, dryness, ultraviolet irradiation, or spray of a specific compound. Examples of such promoters include a promoter for a gene encoding ribulose-1,5-diphosphate carboxylase small subunit which is induced by light irradiation (Fluhr, 1986, Proc. Natl. Acad. Sci. USA 83, 2358), a promoter for rice lip19 gene inducible by low temperature (Aguan, 1993, Mol. Gen. Genet. 240, 1), promoters for rice hsp72 and hsp80 genes inducible by high temperature (Van Breusegem, 1994, Planta 193, 57), a promoter for the rab16 gene of *Arabidopsis thaliana* inducible by dryness (Nundy, 1990, Proc. Natl. Acad. Sci. USA 87, 1406), and a promoter for maize alcohol dehydrogenase gene inducible by ultraviolet irradiation (Schulze-Lefert, 1989, EMBO J. 8, 651). A promoter for the rab16 gene is inducible by spraying abscisic acid which is a plant hormone.

A "terminator" is a sequence which is located downstream of a region encoding a protein of a gene and which is involved in the termination of transcription when DNA is transcribed into mRNA, and the addition of a polyA sequence. It is known that a terminator contributes to the stability of mRNA, and has an influence on the amount of gene expression. Examples of such a terminator include, but are not limited to, a CaMV35S terminator and a terminator for the nopaline synthetase gene (Tnos).

A "drug-resistant gene" is desirably one that facilitates the selection of transformed plants. The neomycin phosphotransferase II (NPTII) gene for conferring kanamycin resistance, the hygromycin phosphotransferase gene for conferring hygromycin resistance, and the like may be preferably used. The present invention is not so limited.

An "enhancer" may be used so as to enhance the expression efficiency of a gene of interest. As such an enhancer, an enhancer region containing an upstream sequence within the CaMV35S promoter is preferable. A plurality of enhancers may be used for certain gene expression.

Plant expression vectors as described above may be prepared using a gene recombination technique well known to those skilled In the art. In addition to vectors used in the Examples below, pBI vectors or pUC vectors are preferably used in construction of a plant expression vector. The present invention is not so limited.

A plant material for DNA introduction can be appropriately selected from leaves, stems, roots, tubers, protoplasts, calluses, pollen, embryos, shoot primordium, according to the introduction method or the like. A "plant cell" may be any plant cell. Examples of a "plant cell" include cells of tissues in plant organs, such as leaves and roots; callus; and suspension culture cells. The plant cell may be in any form of a culture cell, a culture tissue, a culture organ, or a plant. Preferably, the plant cell is a culture cell, a culture tissue, or a culture organ. More preferably, the plant cell is a culture cell.

A plant culture cell, to which DNA is introduced, is generally a protoplast. DNA is introduced to a plant culture cell by a physicochemical method, such as an electroporation method and a polyethylene glycol method. A plant tissue, to which DNA is introduced, is a leaf, a stem, a root, a tuber, a callus, pollen, an embryo, shoot primordium, preferably a leaf, a stem, and a callus. DNA is introduced into a plant tissue by a physicochemical method, such as a biological method using a virus or *Agrobacterium*, or a particle gun method. The method using *Agrobacterium* is disclosed, for example, in Nagel et al. (Microbiol. Lett., 67, 325 (1990)). In this method, a plant expression vector is first used to transform *Agrobacterium* (e.g., by electroporation), and then the transformed *Agrobacterium* is introduced into a plant tissue by a well-known method, such as a leaf disc method. These methods are well known in the art. A method suitable for a plant to be transformed can be appropriately selected.

A cell, into which a plant expression vector has been introduced, is selected for drug resistance, such as kanamycin resistance. The selected cell can be regenerated to a plant by a commonly used method.

A plant cell, into which a polynucleotide of the present invention has been introduced, can be regenerated to a plant by culturing the plant cell in a redifferentiation medium, hormone-free MS medium, or the like. A young rooted plant can be grown to a plant by transferring it to soil, followed by cultivation. Redifferentiation methods vary depending on plant cell types. Redifferentiation methods for various plants are described: rice (Fujimura, 1995, Plant Tissue Culture Lett. 2, 74); maize (Shillito, 1989, Bio/Technol. 7, 581; Gorden-Kamm, 1990, Plant Cell 2, 603); potato (Visser, 1989, Theor. Appl. Genet. 78, 594); and tobacco (Nagata, 1971, Planta 99, 12).

Expression of an introduced gene of the present invention in a regenerated plant can be confirmed by a method well known to those skilled in the art. This confirmation can be carried out using, for example, Northern blotting. Specifically, total RNA is extracted from a plant leaf, subjected to electrophoresis on denaturing agarose, and blotted to an appropriate membrane. This blot is then subjected to hybridization with a labeled RNA probe complementary to a portion of the introduced gene, thereby detecting mRNA of a gene of the present invention.

Plants which can be transformed using a polynucleotide of the present invention include any plant to which a gene can be introduced. As used herein, the term "plant" includes reference to whole plants, plant organs (e.g., leaves, stems, roots, etc.), seeds, plant propagators (e.g., pollen), and plant cells, and progeny of same. Plant cells as used herein include, without limitation, seeds, suspension cultures, embryos, meristematic regions, callus tissue, leaves, roots, shoots, gametophytes, sporophytes, pollen, and microspores. The term "plant" includes monocotyledonous and dicotyledonous plants. Such plants include any useful plants, particularly crop plants, vegetable plants, and flowering plants of garden varieties. Preferable plants include, but are not limited to, rice, maize, sorghum, barley, wheat, rye, *Echinochloa crusgalli*, foxtail millet, asparagus, potato, Japanese white radish, soybean, pea, rapeseed, spinach, tomato, and petunia. The most preferable plant to which the present invention is applied is rice, particularly Japonica rice.

Examples of types of plants that can be used in the manufacturing method of the present invention include plants in the families of Solanaceae, Poaceae (Poaceae; Gramineae), Brassicaceae, Rosaceae, Leguminosae, Curcurbitaceae, Lamiaceae, Liliaceae, Chenopodiaceae and Umbelliferae.

Examples of plants in the Solanaceae family include plants in the *Nicotiana, Solanum, Datura, Lycopersicon* and *Petunia* genera. Specific examples include tobacco, eggplant, potato, tomato, chili pepper, and petunia.

Examples of plants in the Poaeae family include plants in the *Oryza, Hordenum, Secale, Saccharum, Echinochloa* and *Zea* genera. Specific examples include rice, barley, rye, *Echinochloa crus-galli*, sorghum, and maize.

Examples of plants in the Brassicaceae family include plants in the *Raphanus, Brassica, Arabidopsis, Wasabia*, and *Capsella* genera. Specific examples include Japanese white radish, rapeseed, *Arabidopsis thaliana*, Japanese horseradish, and *Capsella bursa-pastoris*.

Examples of plants in the Rosaceae family include plants in the *Orunus, Malus, Pynus, Fragaria*, and *Rosa* genera. Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alfalfa*, and *Medicago* genera. Specific examples include soybean, adzuki bean, kidney bean, pea, fava bean, peanut, clover, and bur clover.

Examples of plants in the Curcurbitaceae family include plants in the *Luffa, Curcurbita*, and *Cucumis* genera. Specific examples include gourd, pumpkin, cucumber, and melon.

Examples of plants in the Lamiaceae family include plants in the *Lavandula, Mentha*, and *Perilla* genera. Specific examples include lavender, peppermint, and beefsteak plant.

Examples of plants in the Liliaceae family include plants in the *Allium, Lilium*, and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia*, and *Apitum* genera. Specific examples include Japanese udo, carrot, honewort, and celery.

The nomenclature used hereafter and the laboratory procedures described hereafter often involve well known and commonly employed procedures in the art. Standard techniques are used for recombinant methods, polynucleotide synthesis, and cell culture. The techniques and procedures are generally performed according to conventional methods in the art and various general references (see, generally, Sambrook et al. Molecular Cloning: A Laboratory Manual, 2nd ed. (1989) Cold Spring Harbor Laboratory Press, Cold Spring Harbor, N.Y., which is incorporated herein by reference).

The present inventions are illustrated in the following Examples, but should not be interpreted as limited thereto. Unless stated otherwise, materials, agents and the like used in the Examples are commercially available.

EXAMPLE

Example 1

Mature seeds of "Nipponbare" cultivar were used as starting material to conduct callus initiation culture and cell suspension culture, as described in Hirochika et al., 1996, Proc. Natl. Acad. Sci. USA, 93, 7783-7788) (supra). Culture conditions for activating Tos17 used in gene disruption were determined in accordance with Otsuki's method (1990) (Rice protoplast culture, Agriculture, Forestry and Fisheries Technical Information Society).

Briefly, the mature seeds of rice were cultured in MS medium containing 2,4-dichlorophenoxyacetic acid (2,4-D) (Otsuki (1990), supra) (25° C., one month) so as to induce calli. The resultant calli were cultured in N6 liquid medium containing 2,4-D (Otsuki (1990), supra) for five months, and were transferred to a redifferentiation medium (Otsuki (1990), supra) to obtain redifferentiated rice (first generation (M1) plant).

The resultant R1 rice individuals were regarded as a plant; their seeds were collected from respective plants. After seeding, the obtained M2 plants were grown and subjected to morphological analysis. Careful observation of phenotype of respective plants in R2 population until about five months after germination indicated that one-third of plants have abnormally increased tillering among R2 population of one line, NE3003 (Cultivar: Nipponbare) (FIG. 1). This suggests that extremely increased tillers in the NE3003 plants were due to recessive mutation at a single locus. FIG. 1 comprise photographs of plant morphology of NE3003 (right) and the corresponding control wild-type (left), which has been grown in paddy fields. The NE3003 plants with extremely increased tillers have narrower, shorter, and thinner leaves than those of the wild-type plants. NE3003 is shown to have a higher number of leaves and roots per individual than those of wild-type. FIG. 2 shows cross sections of leaves from NE3003 (upper) and wild-type (lower). NE3003 plants have inclined angle of leaves, due to the swollen cells in the upper portions of their vascular bundle. Thus, the modification of the subject gene allows regulation of leaf shape such as angles and the like.

Example 2

In order to confirm that the extremely increased tillers in the NE3003 plants were due to recessive mutation at a single locus, genomic DNA was extracted from the respective offspring individuals segregated in phenotype; and Southern hybridizations were conducted using Tos17 as probe.

In brief, genomic DNA was isolated from leaves of M2 rice (NE3003 strain) obtained in Example 1 by using CTAB method (Murray, MG and Thompson, WF, 1981, Nucleic Acids Res., 8, 4321-4325). DNA sample (500 ng) was subjected to appropriate restriction enzymes treatments for digestion, followed by fractionation using 0.8% agarose gel and consequent transfer to positively charged nylon membranes (Amersham, Hybond N+). Tos17 (Hirochika et al, 1992, Mol. Gen. Genet., 233, 209-216) XbaI/BamHI fragments were labeled with $^{32}$P.

Figure 3:
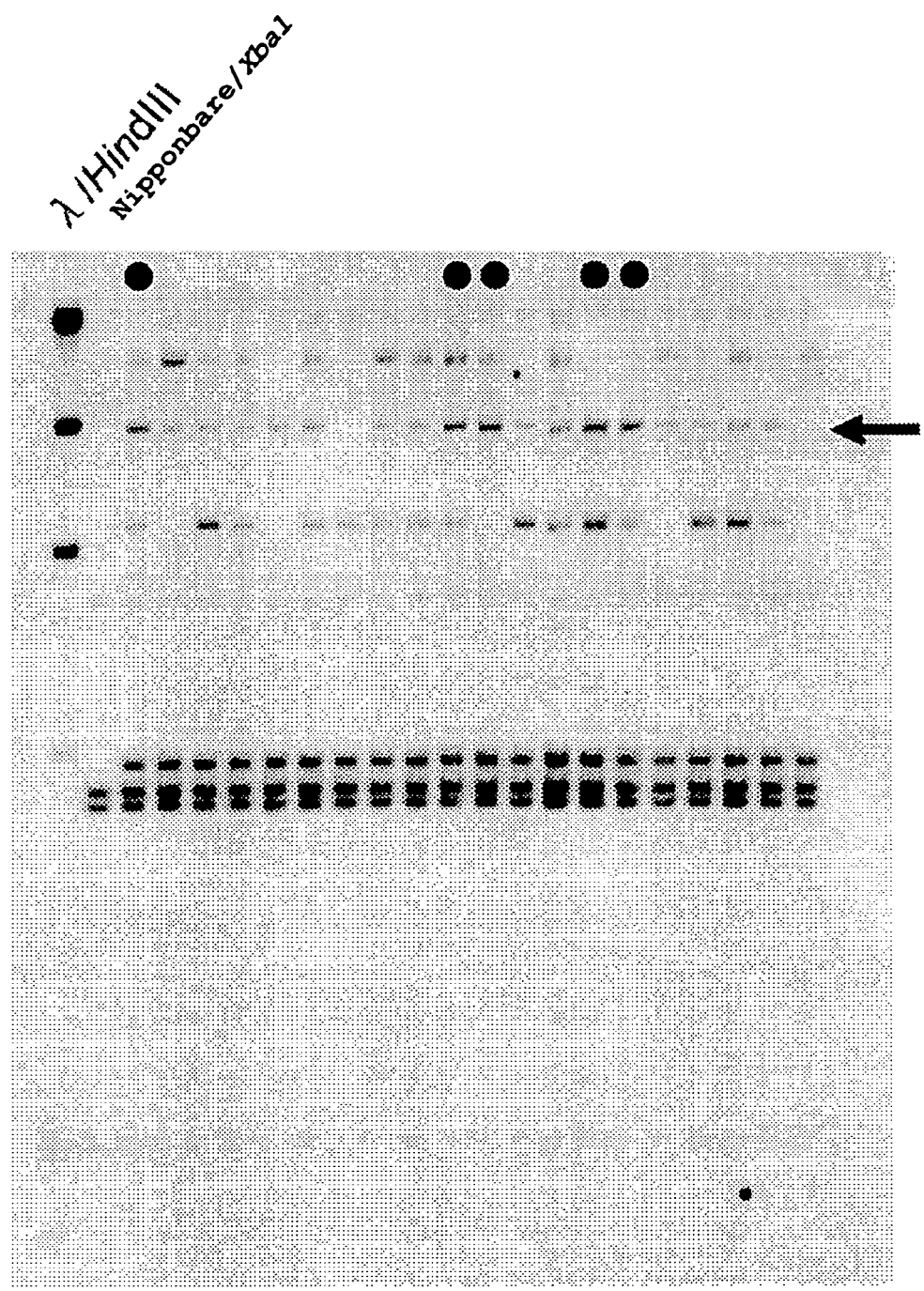
FIG. 3 is the electrophoretogram which indicates a southern analysis result using Tos17 as probe.

The Genomic Southern hybridization was conducted in essentially same manner as described in Sambrook et al, (1989) "Molecular Cloning A Laboratory Manual", Cold Spring Harbour Laboratory Press, Cold Spring Harbor, N.Y. Then the blotting membrane was subjected to hybridization using the above $^{32}$P labeled Tos17 probe, in a buffer containing 0.5M $NaH_2PO_4$, pH7.2, 1 mM EDTA, 7% SDS, 200 µg/ml denatured fetal bovine thymic DNA for overnight at 65° C. Then the blotting membrane was washed with a cleaning buffer (2×SSC, 0.1% SDS), once (1 minute) at room temperature, and once at 55° C. (one hour). 1×SSC contains 0.15M NaCl and 15 mM sodium citrate, pH7.0. The results were indicated in FIG. 3. In FIG. 3, lanes with solid circle correspond to the phenotype expressing enhanced tillering and narrower leaves. In these lanes, darker bands were observed as indicated by the arrow. The results showed linkage between the phenotype and Tos17 band.

Example 3

Suppression PCR was conducted using DNAs as template, wherein the bands of the DNAs corresponded to homozygote mutants and wild-type of southern analysis described in Example 2. The fragments of Tos17 flanking regions were amplified and isolated only when using the mutants as a template.

In brief, DNA was prepared from M2 rice (NE3003 strain and wild type) by using CTAB method (Murray and Thompson, 1980, Nucleic Acids Res. 8, 4321-4325). Tos17 target site sequences were amplified by suppression PCR method (Miyao et al, 1998, Plant Biotech., 15, 253-256).

Briefly, total DNA was extracted from R2 rice regenerated plants (NE3003 strain and wild type) which are segregated in phenotype, by using CTAB method. The DNA was digested with restriction enzyme NruI, and ligated with adapter DNAs (AD-F (SEQ ID NO: 3) and AD-R(SEQ ID NO: 4)) in 3' terminals by using T4 ligase. The ligation reaction was carried out overnight at 16° C. PCR amplification was conducted by using the 1 µl ligation reaction solution as template, a primer having Tos17 terminal base sequence (Tos17-tail3; SEQ ID NO: 7) and a primer having adaptor base sequence (AP-1; SEQ ID NO: 5).

The PCR conditions were indicated in the following:
Pretreatment 94° C., 1 minute;
Amplification reaction 94° C., one minute; 68° C., 6 minutes, totally, 30 cycles;
After treatment 68° C., 7 minutes;

The second PCR amplification was conducted by using 1 µl of 200-fold dilution of the resultant reaction solution as template, a primer having Tos17 terminal base sequence (Tos17-tail5) (SEQ ID NO: 8) and a primer having the adaptor base sequence (AP-2; SEQ ID NO: 6).

The resultant amplification products were subjected to 1.5% agarose electrophoresis, and then the isolated bands were purified by using PCR product purification kit (Promega).

The purified DNA fragments were sequenced by sequencing reaction carried out with BigDye terminator cycle sequence kit (ABI) and 377 type sequencing apparatus (ABI).

Southern hybridizations were conducted using the fragment (SEQ ID NO: 8) as a probe and the membranes described in Example 2. Hybridization results are shown in FIG. 4.

Figure 4:
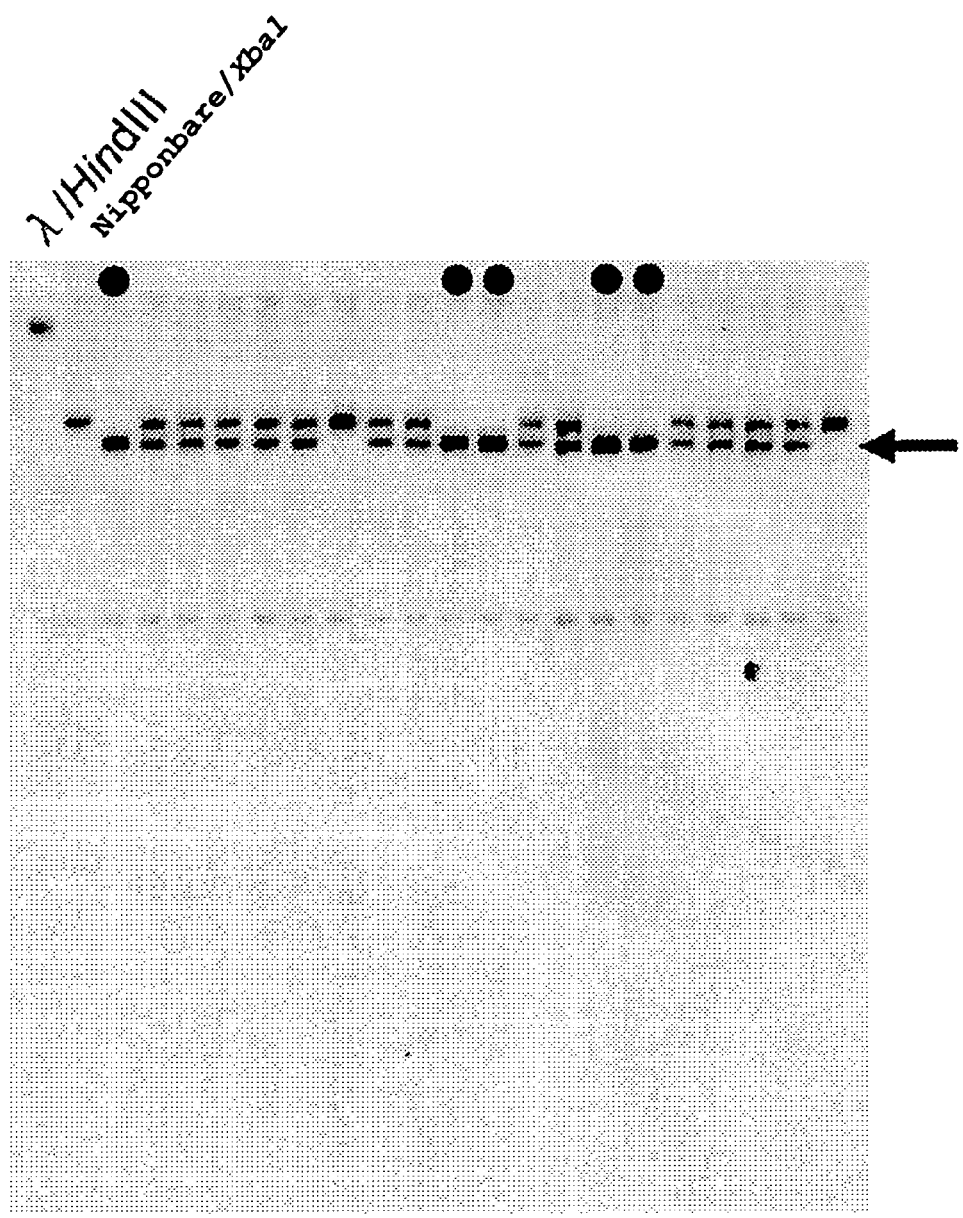
FIG. 4 is an electrophoretogram showing results of southern analysis using cloned candidate genes as probe.

In FIG. 4, the lanes with a solid circle show phenotype having enhanced tillering and narrower leaves. In these lanes, dark bands were observed in the position indicated by the arrow symbol. As shown in FIG. 4, the phenotype segregation observed in Example 2 corresponded to the bands of linked Tos17, strongly suggesting that the gene characterized by cloning was the responsible gene.

Example 4

We then conducted screening of the λ phage library of the Nipponbare by using the fragment isolated in Example 3 as a probe. The genome library of Nipponbare was prepared previously in our laboratory. Briefly, the procedure for preparing the genome library was, first partially digesting the genomic DNA with Sau3AI to obtain fragments from the genome, and then preparing the library by inserting the fragments into EMBL3 vectors (Frischauf et al, 1983, J. Mol. Biol. 170, 827-842). The screening procedure was conducted according the method described in Molecular Cloning, A Laboratory Manual (Sambrook et al, 1989).

Figure 5:
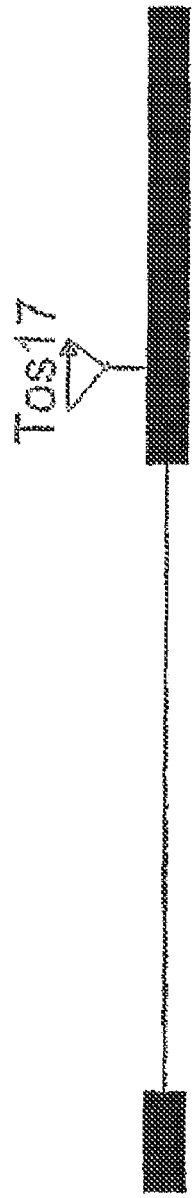
FIG. 5 illustrate the structure of a gene on PAC AP003237 derived from rice species chromosome 1, wherein the gene is similar to hypothetical *Arabidopsis theliana* as well as the location of Tos17 inserted thereto. Heavy bar indicates exon while thin bar indicates intron.

The nucleic acid sequences derived from the genomic DNA were analyzed using the International Rice Genome Sequencing Project to identify homologous regions to the genomic DNA sequences. FIG. 6 indicates the sequence alignments among the sequences. The upper row in the FIG. 6 indicates flanking nucleic acid sequences of the inserted Tos17 nucleic acid sequence (Query, in the FIG. 6). In FIG. 6, the lower nucleic acid sequence represents the region in AP003237 base sequence that is homologous to the nucleic acid sequence where the Tos17 has been inserted (Sbjct in FIG. 6). The first base of the flanking base sequence corresponds to the base next to 3' terminal base of Tos17. FIG. 6 shows that Tos17 has been inserted into the position 112452 portion of AP003237. Thus, the resultant sequence was found to correspond to the base sequence of the published PAC clone AP003237 of rice chromosome 1 (FIG. 6). FIG. 5 shows the PAC clone AP003237 location into which Tos17 is inserted, wherein the AP003237 is derived from rice chromosome 1. The direction of the inserted Tos17 is the same as that of the gene. In FIG. 5, the thicker bar indicates an exon, while the thinner bar indicates intron.

Example 5

The loss-of-function region wherein Tos17 was inserted was found to be a region which possibly encodes a functionally unknown gene, based on the annotation of the rice genomic base sequence obtained from the analysis of Example 4. BLASTX search (Altshul et al. 1997, Nucleic Acids Res., 25, 3389-3402) was conducted against a non-redundant amino acid database of all organisms, "nrtr, which is provided by NCBI. The results of the search identified a genomic base sequence derived from Arabidopsis which corresponded to the query. The sequence alignment of the sequences is shown in FIG. 7. FIG. 7 shows the responsible gene for enhanced tillering in rice (upper) and the corresponding homologous amino acid sequence encoded by a Arabidopsis gene (lower). The detected region was found to be a region which was predicted to encode an unknown functional gene. Accordingly, the isolated gene herein was first analyzed for its function. Then the active domain of the sequence was estimated using a Motif Scan in a Protein Sequence program (available on the worldwide web at hits.isb-si.b.ch/cgi-bin/PFSCAN). As a result, the gene was estimated to have an amino acid motif. GHSLG as promising active domain, which is underlined in FIG. 7.

Example 6

Construction of Complementation Vectors and Transformation in Lesion Mimic Mutant with *Agrobacterium umefaciens*

4525 bp AsuII fragments, which is isolated in Example 4 and derived from EMBL genome clone, was incorporated into pPZP2H-lac vector (pPZP2fine). The pPZP2H-lac vector was provided by Applied Genomics Laboratory Department of Molecular Genetics, National Institute of Agrobiological Science. The recombinant vector was used for transformation of *Agrobacterium tumefaciens* EHA101 strain by using electroporation, followed by selection with 50 mg/l hygromycin. Vectors which do not include the subject gene were introduced as control. The resultant *Agrobacterium* strains were cryopreserved until use.

The seeds were subjected to sterilization treatment in a solution of 1% sodium hypochlorite, followed by washing with sterilized distilled water (×5). The resultant seeds were used for transformation as described in Tanaka et al (Japanese Patent No. 3141084). The seeds had their rice chaff removed, and the resultant intact seeds were subjected to sterilization treatment in a solution of 2.5% sodium hypochlorite (NaClO). After ample cleaning with water, the rice seeds were subjected to the following aseptic manipulations.

The seeds were placed in N6D medium (30 g/l sucrose, 0.3 g/l casamino acids, 2.8 g/l proline, 2 mg/l 2,4-D, 4 g/l gellite, pH5.8), containing 2,4-D, followed by five-day incubation at 28° C.-32° C. During the incubation, the seeds underwent germination.

The above mentioned seeds were soaked in the suspension of the transformed *Agrobacterium*, before being implanted in 2N6-AS medium (30 g/l sucrose, 10 g/l glucose, 0.3 g/l casamino acids, 2 mg/l 2,4-D, 10 mg/l acetosyringone, 4 g/l gellite, pH 5.2), and cocultured in dark for three days at 28° C.

After completion of the coculture, the *Agrobacterium* was flushed from the seeds, with N6D medium containing 500 mg/l carbenicillin. The selection of the transformed seeds was carried out according to the following manner.

The first selection: seeds were placed in N6D medium containing 2 mg/l 2,4-D supplemented with carbenicillin (200 mg/l) and hygromycin (50 mg/l), and incubated for seven days at 27° C.-32° C.

The second selection: seeds were placed in N6D medium containing 2 mg/l 2,4-D supplemented with carbenicillin (200 mg/l) and hygromycin (50 mg/l), and incubated for seven days at 27° C.-32° C.

The selected transformed seeds were allowed to undergo redifferentiation under the following conditions. The first redifferentiation: selected seeds were placed in a redifferentiation medium, MS medium (30 g/l sucrose, 30 g/l sorbitol, 2 g/l casamino acids, 2 mg/l kinetin, 0.002 mg/l NAA, 4 g/l gellite, pH5.8) supplemented with carbenicillin (200 mg/l) and hygromycin (50 mg/l) for two weeks, at 27° C.-32° C.

The second redifferentiation: seed were incubated in the same medium as used in the first redifferentiation for additional two weeks, at 27° C.-32° C. The redifferentinated transformants were moved to a rooting medium which was a MS medium supplemented with hygromycin (50 mg/l), but free from hormone. After confirmation of development of roots, the plants were moved to the field.

Figure 8:
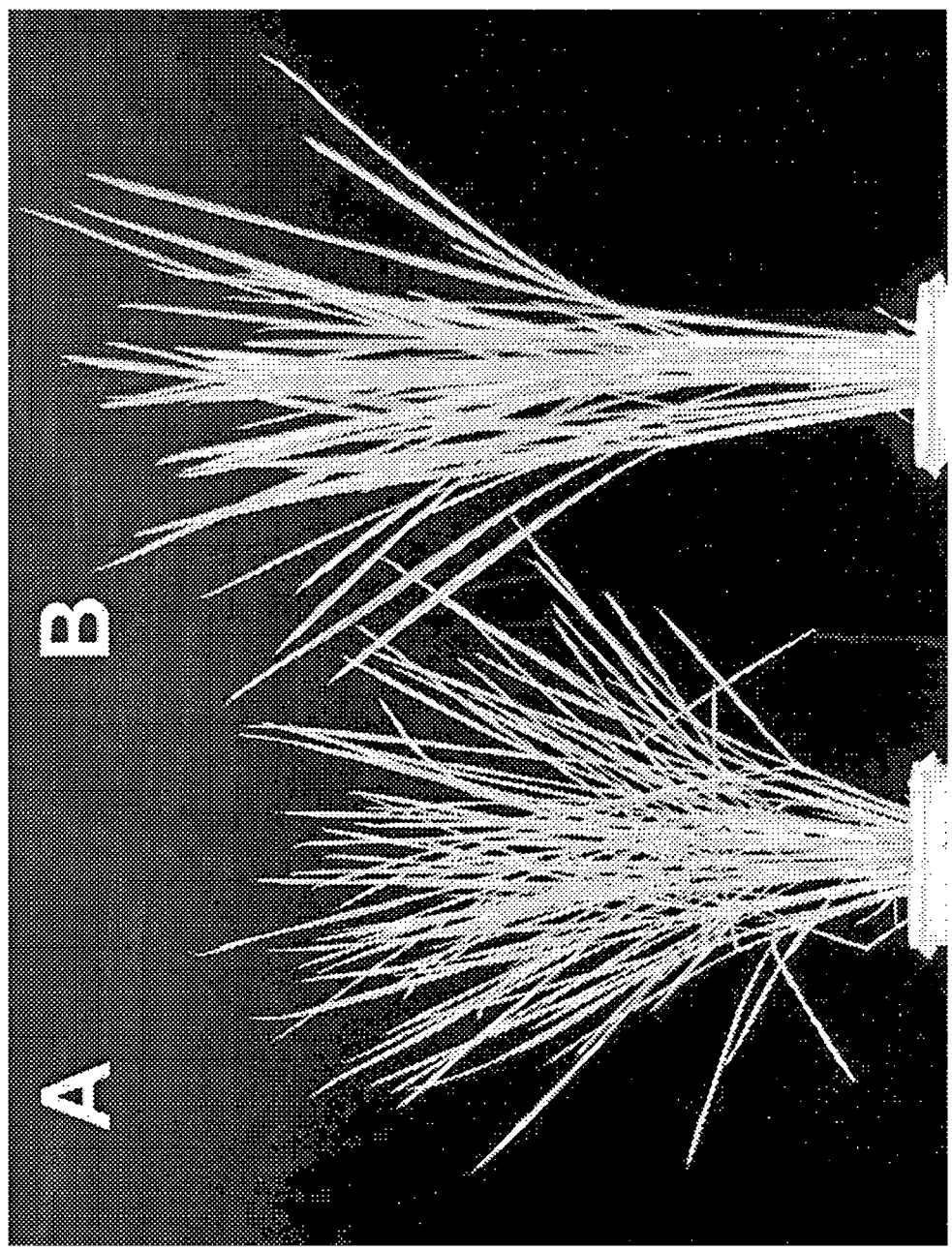
FIG. 8 shows a photograph showing plant habits of NE3003 strains, which have pPZP2H-lac (control; panel A) or complement vector (pZPZ2fine) (panel B) prepared in Example 6.

The results are shown in FIG. 8. NE3003 strain (panel B) into which the corresponding complementation vectors (pPZP2Hfine) was introduced, had the same phenotype as that of wild-type, demonstrating that the mutation in the subject gene is the cause of the enhanced tillering in the plant.

INDUSTRIAL APPLICABILITY

Tillering and leaf morphology are important characters which have an significant consequence for photosynthetic efficiency, lodging resistance, yield and the like. In the present loss-function mutants, the increased tillering and altered shapes of leaves were observed. The modification in expression amount and timing of responsible gene or the modification of the amino acid sequence encoding the gene allows the control of the tillering and the morphology of leaves, thereby increasing the yield per individual plant. In addition, the loss-function mutants of the corresponding gene in a turfgrass, herbage or the like which belongs to Poaceae family, allows increased amounts of the leaves per unit area, efficient applications of the techniques to animal industry. Increased or decreased tillering provided by the present invention allows production of valuable decorative plants.

The invention claimed is:

1. A method for controlling tillering and leaf morphology in a plant, the method comprising:
   introducing an isolated polynucleotide into a plant cell, wherein the polynucleotide encodes a plant gene capable of controlling tillering and leaf morphology in the plant, wherein the polynucleotide includes a nucleotide sequence encoding an amino acid sequence from methionine (Met) at position 1 to lysine (Lys) at position 411 of SEQ ID NO: 2; or a nucleotide sequence encoding an amino acid sequence having at least 95% sequence identity to the amino acid sequence from methionine (Met) at position 1 to lysine (Lys) at position 411 of SEQ ID NO: 2, and is capable of controlling tillering and leaf morphology in the plant; and
   regenerating the plant cell to obtain a plant whose tillering and leaf morphology is controlled.

2. The method according to claim 1, wherein the plant is a monocotyledon.

3. The method according to claim 2, wherein the monocotyledon is a Gramineae plant.

4. The method according to claim 2, where the Gramineae plant is rice.

5. The method according to claim 1, wherein the plant is a dicotyledon.

6. A method for controlling tillering and leaf morphology in a plant, the method comprising the steps of: introducing an isolated polynucleotide into cells of the plant, wherein the polynucleotide has a nucleotide sequence from A at position 148 to G at position 1383 of SEQ ID NO:1; or a nucleotide sequence having at least 95% sequence identity to the nucleotide sequence from A at position 148 to G at position 1383 of SEQ ID NO:1;
   and
   regenerating the plant cell to obtain a plant whose tillering and leaf morphology is controlled.

7. The method according to claim 6, wherein the plant is a monocotyledon.

8. The method according to claim 7, wherein the monocotyledon is a Gramineae plant.

9. The method according to claim 8, wherein the Gramineae plant is rice.

10. The method according to claim 9, wherein the plant is dicotyledon.

* * * * *

SEQUENCE LISTING

<160> NUMBER OF SEQ ID NOS: 13

<210> SEQ ID NO 1
<211> LENGTH: 1553
<212> TYPE: DNA
<213> ORGANISM: Oryza sativa

<400> SEQUENCE: 1

```
acgattcgtc gcgttcgcgt gctgccaaat cctcctcccc ctcctccgtc cccacaacat      60
tctgtcgcgc cgattcgacc gttgccgcct cgcccgctcc gcgcacgcgc gcacgccgct     120
cccgttcccc tcgcgcacgc gcgggccatg gcgatcgacc tggcgccgct ggctggggag     180
ttggaggtcg cgggggcggc ggttggaggg aagaagaggg aggggggaggg ggaggagggc     240 ggggtgtgcg gcggggaggc cgtggtggtg gccgcggcgg acgcggaggt ggagggccac     300
ccctacgact ccacgtgtc cgggccgcgg aacctgccgc cgcccaactg gagggagatc     360
atccgttcga gctggaagga tcccaattac aaaaggatgg taatggcctg cttcattcaa     420
gcagtctacc tgcttgaact ggacaggcaa gatgagaaag gagaagagga tggccttgct     480
ccaaaatggt ggaagcccctt caaatacaag gtcacacaga cattggtcga tgagagagat     540
ggttccatct atggtgccgt ccttgagtgg gatcgttctt ctgctttgtc tgaccttatc     600
ctcataagac caagtggcgc gccaagggct gtgttagctc tccgaggaac actgcttcag     660
aagcccacca tcaagagaga cctacaagat gatcttcgct tcctggtgtg ggagagctta     720
aaaggatcag tcagatatat tggcgcttta gaagcactga agacagcagt tgagaggttt     780
ggtagcgcta atgtcagtgt tgctgggcac tccttgggag ctggatttgc tcttcaggtt     840
tgcaaagagc tcgctaagca aggagtcttc gtggagtgtc atctgttcaa tccaccttct     900
gtttcacttg ccatgggtgt aaggagtatg agtgagaagg ccagctacct gtggaaaaaa     960
gttaaggcta gtctaccact gactgaagaa gcattacctg acagtaccaa agaggaggga    1020
agtgcaaaga agaaattgcg tgctgacaag aaatgggtgc cacatttata tgtaaacaac    1080
agtgactaca tctgctgtca ctacaatgcc cctaattgct ccaccaccac caccactacc    1140
```

```
accactgatg gtgcttcaga tgagcagcag cagcaacgaa aggcaagtga gatcgctggt    1200
gatgtggtcg cgaagctttt tgtgacatcg aaaggcccac agaagtttct tgaagcgcat    1260
gggctggagc aatggtggtc ggatggcatg gagctgcagc tagcagtgta tgacagcaag    1320
cttatataca ggcagttgaa gtccctctac acagcaactg caccgtcacc ccctgcaaag    1380
tagtagaaac tgctgagatc gctgtttcaa ctggcgttag aaatactctt tctaatcagt    1440
ttctgcctct attaacttga tatgtttcat catggttgtg actgtgaact attatacagt    1500
aaaatataat aaacggacat gtgctgataa atacattgat attttcatg ttc            1553
```

<210> SEQ ID NO 2
<211> LENGTH: 411
<212> TYPE: PRT
<213> ORGANISM: Oryza sativa

<400> SEQUENCE: 2

```
Met Ala Ile Asp Leu Ala Pro Leu Ala Gly Glu Leu Glu Val Ala Gly
1               5                   10                  15

Ala Ala Val Gly Gly Lys Lys Glu Glu Gly Glu Gly Glu Gly Gly
            20                  25                  30

Val Cys Gly Gly Glu Ala Val Val Ala Ala Ala Asp Ala Glu Val
        35                  40                  45

Glu Gly His Pro Tyr Asp Phe His Val Ser Gly Pro Arg Asn Leu Pro
    50                  55                  60

Pro Pro Asn Trp Arg Glu Ile Ile Arg Ser Ser Trp Lys Asp Pro Asn
65                  70                  75                  80

Tyr Lys Arg Met Val Met Ala Cys Phe Ile Gln Ala Val Tyr Leu Leu
                85                  90                  95

Glu Leu Asp Arg Gln Asp Glu Lys Gly Glu Glu Asp Gly Leu Ala Pro
            100                 105                 110

Lys Trp Trp Lys Pro Phe Lys Tyr Lys Val Thr Gln Thr Leu Val Asp
        115                 120                 125

Glu Arg Asp Gly Ser Ile Tyr Gly Ala Val Leu Glu Trp Asp Arg Ser
    130                 135                 140

Ser Ala Leu Ser Asp Leu Ile Leu Ile Arg Pro Ser Gly Ala Pro Arg
145                 150                 155                 160

Ala Val Leu Ala Leu Arg Gly Thr Leu Leu Gln Lys Pro Thr Ile Lys
                165                 170                 175

Arg Asp Leu Gln Asp Asp Leu Arg Phe Leu Val Trp Glu Ser Leu Lys
            180                 185                 190

Gly Ser Val Arg Tyr Ile Gly Ala Leu Glu Ala Leu Lys Thr Ala Val
        195                 200                 205

Glu Arg Phe Gly Ser Ala Asn Val Ser Val Ala Gly His Ser Leu Gly
    210                 215                 220

Ala Gly Phe Ala Leu Gln Val Cys Lys Glu Leu Ala Lys Gln Gly Val
225                 230                 235                 240

Phe Val Glu Cys His Leu Phe Asn Pro Pro Ser Val Ser Leu Ala Met
                245                 250                 255

Gly Val Arg Ser Met Ser Glu Lys Ala Ser Tyr Leu Trp Lys Lys Val
            260                 265                 270

Lys Ala Ser Leu Pro Leu Thr Glu Glu Ala Leu Pro Asp Ser Thr Lys
        275                 280                 285

Glu Glu Gly Ser Ala Lys Lys Lys Leu Arg Ala Asp Lys Lys Trp Val
    290                 295                 300
```

| | | | | | | | | | | | | | |
|---|---|---|---|---|---|---|---|---|---|---|---|---|---|
|Pro|His|Leu|Tyr|Val|Asn|Asn|Ser|Asp|Tyr|Ile|Cys|Cys|His|Tyr|Asn|
|305| | | | |310| | | | |315| | | | |320|

Ala Pro Asn Cys Ser Thr Thr Thr Thr Thr Thr Thr Asp Gly Ala
                 325                      330                     335

Ser Asp Glu Gln Gln Gln Gln Arg Lys Ala Ser Glu Ile Ala Gly Asp
          340                    345                   350

Val Val Ala Lys Leu Phe Val Thr Ser Lys Gly Pro Gln Lys Phe Leu
        355                    360                   365

Glu Ala His Gly Leu Glu Gln Trp Trp Ser Asp Gly Met Glu Leu Gln
 370                  375                    380

Leu Ala Val Tyr Asp Ser Lys Leu Ile Tyr Arg Gln Leu Lys Ser Leu
385                  390                    395                  400

Tyr Thr Ala Thr Ala Pro Ser Pro Pro Ala Lys
             405                    410

<210> SEQ ID NO 3
<211> LENGTH: 44
<212> TYPE: DNA
<213> ORGANISM: Artificial sequence
<220> FEATURE:
<223> OTHER INFORMATION: synthetic AD-F DNA fragment

<400> SEQUENCE: 3
ctaatacgac tcactatagg gctcgagcgg ccgcccgggc aggt                   44

<210> SEQ ID NO 4
<211> LENGTH: 8
<212> TYPE: DNA
<213> ORGANISM: Artificial sequence
<220> FEATURE:
<223> OTHER INFORMATION: synthetic AD-R DNA fragment

<400> SEQUENCE: 4 acctgccc                                                                      8

<210> SEQ ID NO 5
<211> LENGTH: 27
<212> TYPE: DNA
<213> ORGANISM: Artificial sequence
<220> FEATURE:
<223> OTHER INFORMATION: synthetic AP-1 DNA fragment

<400> SEQUENCE: 5
ggatcctaat acgactcact atagggc                                    27

<210> SEQ ID NO 6
<211> LENGTH: 17
<212> TYPE: DNA
<213> ORGANISM: Artificial sequence
<220> FEATURE:
<223> OTHER INFORMATION: synthetic AP-2 DNA fragment

<400> SEQUENCE: 6
aatagggctc gagcggc                                               17

<210> SEQ ID NO 7
<211> LENGTH: 26
<212> TYPE: DNA
<213> ORGANISM: Artificial sequence
<220> FEATURE:
<223> OTHER INFORMATION: synthetic Tos17-tail3 DNA fragment

<400> SEQUENCE: 7
gagagcatca tcggttacat cttctc                                     26

<210> SEQ ID NO 8
<211> LENGTH: 21
<212> TYPE: DNA
<213> ORGANISM: Artificial sequence
<220> FEATURE:
<223> OTHER INFORMATION: synthetic Tos17-tail5 DNA fragment

<400> SEQUENCE: 8
catcggatgt ccagtccatt g                                              21

<210> SEQ ID NO 9
<211> LENGTH: 624
<212> TYPE: DNA
<213> ORGANISM: Artificial sequence
<220> FEATURE:
<223> OTHER INFORMATION: synthetic amplified DNA fragment

<400> SEQUENCE: 9
tgtctgacct tatcctcata agaccaagtg gcgcgccaag ggctgtgtta gctctccgag     60
gaacactgct tcagaagccc accatcaaga gagacctaca agatgatctt cgcttcctgg   120
tgtgggagag cttaaaagga tcagtcagat atattggcgc tttagaagca ctgaagacag   180
cagttgagag gtttggtagc gctaatgtca gtgttgctgg gcactccttg ggagctggat   240
ttgctcttca ggtttgcaaa gagctcgcta agcaaggagt cttcgtggag tgtcatctgt   300
tcaatccacc ttctgtttca cttgccatgg gtgtaaggag tatgagtgag aaggccagct   360
acctgtggaa aaaagttaag gctagtctac cactgactga agaagcatta cctgacagta   420
ccaaagagga gggaagtgca aagaagaaat tgcgtgctga caagaaatgg gtgccacatt   480
tatatgtaaa caacagtgac tacatctgct gtcactacaa tgcccctaat tgctccacca   540
ccaccaccac taccaccact gatggtgctt cagatgagca gcagcagcaa cgaaaggcaa   600
gtgagatcgc tggtgatgtg gtcg                                          624

<210> SEQ ID NO 10
<211> LENGTH: 496
<212> TYPE: DNA
<213> ORGANISM: Artificial sequence
<220> FEATURE:
<223> OTHER INFORMATION: synthetic sequence flanking insertion site of
      Tos17
<220> FEATURE:
<221> NAME/KEY: misc_feature
<222> LOCATION: (161)...(168)
<223> OTHER INFORMATION: n = A,T,C or G
<220> FEATURE:
<221> NAME/KEY: misc_feature
<222> LOCATION: (441)
<223> OTHER INFORMATION: n = A,T,C or G

<400> SEQUENCE: 10
tgtctgacct tatcctcata agaccaagtg gcgcgccaag ggctgtgtta gctctccgag     60
gaacactgct tcagaagccc accatcaaga gagacctaca agatgatctt cgcttcctgg   120
tgtgggagag cttaaaagga tcagtcagat atattggcgc nnnnnnnnca ctgaagacag   180
cagttgagag gtttggtagc gctaatgtca gtgttgctgg gcactccttg ggagctggat   240
ttgctcttca ggtttgcaaa gagctcgcta agcaaggagt cttcgtggag tgtcatctgt   300
tcaatccacc ttctgtttca cttgccatgg gtgtaaggag tatgagtgag aaggccagct   360
acctgtggaa aaaagttaag gctagtctac cactgactga agaagcatta cctgacagta   420
ccaaagagga gggaagtgca nagaagaaat tgcgtgctga caagaaatgg gtgccacatt   480

```
tatatgtaaa caacag                                                     496
```

<210> SEQ ID NO 11
<211> LENGTH: 496
<212> TYPE: DNA
<213> ORGANISM: Artificial sequence
<220> FEATURE:
<223> OTHER INFORMATION: Oryza sativa AP003237 chromosome 1 PAC

<400> SEQUENCE: 11

```
tgtctgacct tatcctcata agaccaagtg gcgcgccaag ggctgtgtta gctctccgag     60
gaacactgct tcagaagccc accatcaaga gagacctaca agatgatctt cgcttcctgg   120
tgtgggagag cttaaaagga tcagtcagat atattggcgc tttagaagca ctgaagacag   180
cagttgagag gtttggtagc gctaatgtca gtgttgctgg gcactccttg ggagctggat   240
ttgctcttca ggtttgcaaa gagctcgcta agcaaggagt cttcgtggag tgtcatctgt   300
tcaatccacc ttctgtttca cttgccatgg gtgtaaggag tatgagtgag aaggccagct   360
acctgtggaa aaaagttaag gctagtctac cactgactga agaagcatta cctgacagta   420
ccaaagagga gggaagtgca agaagaaat tgcgtgctga caagaaatgg gtgccacatt    480
tatatgtaaa caacag                                                    496
```

<210> SEQ ID NO 12
<211> LENGTH: 411
<212> TYPE: PRT
<213> ORGANISM: Oryza sativa Japonica

<400> SEQUENCE: 12

```
Met Ala Ile Asp Leu Ala Pro Leu Ala Gly Glu Leu Glu Val Ala Gly
1               5                   10                  15

Ala Ala Val Gly Gly Lys Lys Glu Glu Gly Glu Gly Glu Glu Gly Gly
            20                  25                  30

Val Cys Gly Gly Glu Ala Val Val Ala Ala Ala Asp Ala Glu Val
        35                  40                  45

Glu Gly His Pro Tyr Asp Phe His Val Ser Gly Pro Arg Asn Leu Pro
    50                  55                  60

Pro Pro Asn Trp Arg Glu Ile Ile Arg Ser Ser Trp Lys Asp Pro Asn
65                  70                  75                  80

Tyr Lys Arg Met Val Met Ala Cys Phe Ile Gln Ala Val Tyr Leu Leu
                85                  90                  95

Glu Leu Asp Arg Gln Asp Glu Lys Gly Glu Glu Asp Gly Leu Ala Pro
            100                 105                 110

Lys Trp Trp Lys Pro Phe Lys Tyr Lys Val Thr Gln Thr Leu Val Asp
        115                 120                 125

Glu Arg Asp Gly Ser Ile Tyr Gly Ala Val Leu Glu Trp Asp Arg Ser
    130                 135                 140

Ser Ala Leu Ser Asp Leu Ile Leu Ile Arg Pro Ser Gly Ala Pro Arg
145                 150                 155                 160

Ala Val Leu Ala Leu Arg Gly Thr Leu Leu Gln Lys Pro Thr Ile Lys
                165                 170                 175

Arg Asp Leu Gln Asp Asp Leu Arg Phe Leu Val Trp Glu Ser Leu Lys
            180                 185                 190

Gly Ser Val Arg Tyr Ile Gly Ala Leu Glu Ala Leu Lys Thr Ala Val
        195                 200                 205

Glu Arg Phe Gly Ser Ala Asn Val Ser Val Ala Gly His Ser Leu Gly
    210                 215                 220
```

```
Ala Gly Phe Ala Leu Gln Val Cys Lys Glu Leu Ala Lys Gln Gly Val
225                 230                 235                 240

Phe Val Glu Cys His Leu Phe Asn Pro Pro Ser Val Ser Leu Ala Met
            245                 250                 255

Gly Val Arg Ser Met Ser Glu Lys Ala Ser Tyr Leu Trp Lys Lys Val
        260                 265                 270

Lys Ala Ser Leu Pro Leu Thr Glu Glu Ala Leu Pro Asp Ser Thr Lys
    275                 280                 285

Glu Glu Gly Ser Ala Lys Lys Lys Leu Arg Ala Asp Lys Lys Trp Val
290                 295                 300

Pro His Leu Tyr Val Asn Asn Ser Asp Tyr Ile Cys Cys His Tyr Asn
305                 310                 315                 320

Ala Pro Asn Cys Ser Thr Thr Thr Thr Thr Thr Thr Asp Gly Ala
            325                 330                 335

Ser Asp Glu Gln Gln Gln Gln Arg Lys Ala Ser Glu Ile Ala Gly Asp
            340                 345                 350

Val Val Ala Lys Leu Phe Val Thr Ser Lys Gly Pro Gln Lys Phe Leu
            355                 360                 365

Glu Ala His Gly Leu Glu Gln Trp Trp Ser Asp Gly Met Glu Leu Gln
370                 375                 380

Leu Ala Val Tyr Asp Ser Lys Leu Ile Tyr Arg Gln Leu Lys Ser Leu
385                 390                 395                 400

Tyr Thr Ala Thr Ala Pro Ser Pro Ala Lys
                    405                 410

<210> SEQ ID NO 13
<211> LENGTH: 358
<212> TYPE: PRT
<213> ORGANISM: Arabidopsis thaliana

<400> SEQUENCE: 13

Met Ala Ser Asp Arg Glu Glu Phe Asn Leu Cys Gly Pro Thr His Leu
1               5                   10                  15

Thr Thr Val Asp Trp Gly Asn Glu Asp His Gln Arg Cys Val Ala Ala
            20                  25                  30

Cys Leu Val Gln Gly Ile Tyr Ile Val Glu Gln Asp Arg Gln Leu Lys
        35                  40                  45

Arg Glu Gly Thr Glu Ala Leu Ala Ser Pro Trp Trp Glu Ser Phe Asn
    50                  55                  60

Phe Lys Leu Ile Arg His Leu Lys Asp Asp Ala Asp Phe Ser Ile Phe
65                  70                  75                  80

Gly Gly Ile Phe Glu Tyr Lys Ser Leu Gln Pro Asp Val Val Asp Ser
                85                  90                  95

Gly Val Pro Arg Tyr Val Ile Ala Phe Arg Gly Thr Leu Thr Lys Ala
            100                 105                 110

Asp Ser Ile Thr Arg Asp Ile Glu Leu Asp Ile His Ile Ile Arg Asn
        115                 120                 125

Gly Leu His Arg Thr Ser Arg Phe Glu Ile Ala Met Gln Ala Val Arg
    130                 135                 140

Ser Met Ala Asp Ser Val Gly Ala Ser Ser Phe Trp Leu Thr Gly His
145                 150                 155                 160

Ser Leu Gly Ala Ala Met Ala Leu Leu Ala Gly Lys Thr Met Gly Lys
                165                 170                 175

Ser Gly Val Tyr Ile Lys Ser Leu Leu Phe Asn Pro Pro Tyr Val Ser
            180                 185                 190
```

-continued

```
Pro Pro Ile Glu Arg Ile Ala Asn Glu Arg Val Arg His Gly Ile Arg
        195             200             205
Phe Ala Gly Ser Leu Ile Thr Ala Gly Leu Ala Leu Ser Arg Thr Leu
        210             215             220
Lys Gln Thr Gln Gln Pro Gln Gln Gln Leu Gln Leu Gln Asn Leu
225             230             235             240
Thr Glu Asp Pro Leu Glu Ala Leu Ser Ser Trp Leu Pro Asn Ile His
                245             250             255
Val Asn Pro Gly Asp His Leu Cys Ser Glu Tyr Ile Gly Phe Phe Glu
                260             265             270
His Arg Gly Asn Met Glu Gln Ile Gly Tyr Gly Ala Gly Ile Val Glu
        275             280             285
Arg Met Ala Met Gln His Ser Leu Gly Gly Leu Leu Met Asp Ala Met
        290             295             300
Gly Val Ser Asn Ala Val Glu Val Glu Glu Pro Val His Val Ile Pro
305             310             315             320
Ser Ala Asn Leu Ile Val Asn Lys Thr Ile Ser Glu Asp Tyr Lys Asp
                325             330             335
Ala His Gly Ile His Gln Trp Trp Arg Asp Asp Gln Asp Leu Val Ser
                340             345             350
His Ile Tyr Met Tyr Lys
        355
```